United States Patent [19]

Hornes et al.

[11] Patent Number: 5,525,493
[45] Date of Patent: Jun. 11, 1996

[54] CLONING METHOD AND KIT

[75] Inventors: Erik Hornes, Oslo, Norway; Mathias Uhlen, Upsala, Sweden

[73] Assignee: Dynal A/S, Oslo, Norway

[21] Appl. No.: 849,389

[22] PCT Filed: Nov. 20, 1990

[86] PCT No.: PCT/EP90/02013

§ 371 Date: May 19, 1992

§ 102(e) Date: May 19, 1992

[87] PCT Pub. No.: WO91/07505

PCT Pub. Date: May 30, 1991

[30] Foreign Application Priority Data

Nov. 21, 1989 [GB] United Kingdom .................. 8926269

[51] Int. Cl.$^6$ .............................. C12Q 1/68; C12N 15/63
[52] U.S. Cl. ...................... 435/91.2; 435/172.3
[58] Field of Search .................. 435/6, 91, 91.2, 435/172.3; 935/77, 78

[56] References Cited

U.S. PATENT DOCUMENTS 4,734,363  3/1988  Dattagupta et al. .................. 435/91

FOREIGN PATENT DOCUMENTS

| 0139489 | 5/1985 | European Pat. Off. | 435/6 |
| 0198662 | 10/1986 | European Pat. Off. | 435/6 |
| 0200362 | 12/1986 | European Pat. Off. | 435/6 |
| 0258017 | 3/1988 | European Pat. Off. | 435/6 |
| 0265293 | 4/1988 | European Pat. Off. | 435/6 |
| 0297379 | 1/1989 | European Pat. Off. | 435/6 |
| 0357011 | 3/1990 | European Pat. Off. | |
| WO85/04663 | 10/1985 | WIPO | 435/6 |
| WO90/06043 | 6/1990 | WIPO | 435/6 |

OTHER PUBLICATIONS

Delius et al., Nuc Acids Res. 13(15):5457–5469 (1985).
Higuchi et al., Nuc Acids Res. 16(15):7351–7367 (1988).
Jovin et al., J. Biol. Chem. 243(2):250–259 (Jan. 25, 1968).
Mullis et al., Cold Sprg Harb. Symp. Quant. Biol. LI: 263–273 (1986).
Venetianer et al., PNAS, USA 71(10):3892–3895 (Oct. 1974).
A. Syvänen et al *Febs Letters,* vol. 258, No. 1, pp. 71–74, Nov. 1989.
C. Aslanidis et al, *Nucleic Acids Research,* vol. 18, No. 20, pp. 6069–6074, Oct. 1990.
T. Hultman et al, *Nucleic Acids Research,* vol. 18, No. 17, pp. 5107–5112, Sep. 1990.

*Primary Examiner*—Stephanie W. Zitomer
*Attorney, Agent, or Firm*—Foley & Lardner

[57] ABSTRACT

A method of amplifying target DNA is disclosed wherein said DNA is first amplified by PCR, the amplified DNA then being contacted with a single stranded linearised plasmid vector having terminal regions which are complementary to terminal regions of the PCR amplified DNA, whereby a cyclic product is formed comprising single stranded sequences from said target DNA and said vector and two double stranded regions from the overlapping terminal regions of the vector and the PCR amplified DNA; the cyclic product then being introduced into a host organism. Two-stage PCR may be performed and site-specific mutagenesis may be effected between PCR amplification and formation of the cyclic product. The single-stranded linearised plasmid vector and/or the target DNA may be immobilised. Kits are disclosed for performing various aspects of the method which can be used in a method of diagnosis wherein the target DNA is characteristic of a physiological condition.

14 Claims, 5 Drawing Sheets

```
3615    RIT113    |pUC handle seq 1|                    |RIT125
        AAGGAGTTGAAGGCCTACAAAT CGGAACTGGA AGAACAACTGACCCCGGTGGCG AGGAGACGCGGGCACGGCTGTCCAAGGAG
        LysGluLeuLysAlaTyrLysLysAlaTyrLysSerGluLeuGluGluGlnLeuThrProValAlaGluGluThrArgAlaArgLeuSerLysGlu
```

```
3700
                                                    T
        CTGCAGGCGGGCAGGCCCCGCTGGGCGCGGACATGGAGGACGTGCGGCGCCTGGTGCGCGCCGGGCGAGGTGCAGGCC
        LeuGlnAlaAlaGlnAlaArgLeuLeuArgLeuAlaAspMetGluAspValArgArgLeuValArgAlaGlyGluValGlnAla
                                                    Cys
                                                    112
```

```
3784
        ATGCTCGGCCAGAGCACCGAGGAGCTGGGCTGCGCCTCCCACCTGCGCAAGCTGCGTAAGCGGCTCCTCCGGATGCC
        MetLeuGlyGlnSerThrGluGluLeuArgValArgLeuAlaSerHisLeuArgLysArgLeuLeuArgAspAla
```

```
3868                                        RIT123                           |pUC handle seq 2|Biotin| RIT114
        GATGACCTGCAGAAGCGCCTGGCA TGTACCAGGCCGGGCGGGCCGGGCGCGGAGGGCGCTCAGGCCATC GC
        AspAspLeuGlnLysArgLeuAlaValTyrGlnAlaGlyAlaArgGluGlyAlaArgGlyLeuAlaArgAlaIleArg
                                 Cys
                                 158
```

CLONING METHOD AND KIT

This invention relates to a cloning method and to a kit for performing same.

The ability to splice genes, gene fragments or other target DNA into vectors or other pieces of DNA using restriction enzymes (RE) and ligases has been an important aspect in the advance of molecular biology and biotechnology. However, the technology of recombination or gene splicing has several disadvantages. Firstly, there is the need for conveniently situated restriction sites and often sites have to be constructed which not only takes time but can lead, in the long term, to mismatched reading frames and for example non-expression of a gene of interest. Such sites are usually introduced by means of oligonucleotide linkers which have to be synthesised and purified and are then used in excess to ensure the addition of the required RE sites(s) on to the target DNA. Secondly, the in vitro ligation or splicing of DNA is rather inefficient and relatively cumbersome screening techniques are required to locate desired recombinants. Finally, the technology is time-consuming and is not well-suited to automation. Accordingly, there is a need for a simple and relatively rapid method of cloning which avoids the problems of conventional splicing and the use of conventional plasmids.

It should be noted that conventional plasmids for cloning normally take the form of double stranded cyclic plasmid structures containing a promoter region separated from a gene or other DNA sequence of interest for replication or expression by one or more RE sites which permit the DNA of interest to be excised subsequently; such sites are also used for insertion of the DNA of interest for replication or expression, via one or more (RE) sites in the linearised plasmid which permit the introduction of DNA of interest, which is provided with 'sticky ends' corresponding to RE sites of the linearised plasmid. When DNA has been synthesised, for example by cDNA synthesis from mRNA, by mutagenesis or by chemical synthesis, it is in single stranded form which is then conventionally treated with a polymerase to synthesise the second strand, provided with the required 'sticky ends', inserted into the double stranded plasmid vector and ligated to join covalently the insert to the vector which is then used to transform a host microorganism, e.g. *E. Coli*.

In recent years, the polymerase chain reaction (PCR) has been used for the amplification of target DNA. While this produces increased amounts of the DNA, it is often required to produce larger quantities by cloning in a suitable vector using a host microorganism such as *E. Coli*. Furthermore, for production of the corresponding protein it is required to incorporate the DNA into an expression vector.

For the reasons given above, conventional techniques for splicing the target gene into plasmid vectors are time consuming and inefficient and not well suited to automation. In cases where PCR itself is effected by an automated technique, it would be desirable for incorporation into the vector also to be readily added on to the automated system.

The present invention has as an object a method which provides for the formation of recombinant DNA from PCR amplified DNA without the need for restriction enzymes or ligases or the provision of restriction sites.

Accordingly, the present invention provides, in one aspect thereof, a method of amplifying target DNA wherein said DNA is first amplified by PCR, the amplified DNA then being contacted with a single stranded linearised plasmid vector having terminal which are complementary to terminal regions of the PCR amplified DNA, whereby a cyclic product is formed comprising single stranded sequences from said target DNA and said vector and two double stranded regions from the overlapping terminal regions of the vector and the PCR amplified DNA; the cyclic product then being introduced into a host organism.

It is surprising that the cyclic product can be used to transform a host directly; the native enzyme system of the host organism is capable of chain extension to complete synthesis of the double stranded plasmid which is then available for replication and/or expression of the DNA of interest.

An advantage of the method according to the invention over conventional PCR is that the target DNA is first amplified by PCR sufficiently to give enough DNA for practical purposes of transformation of a host. The host cell replicates the target DNA quite rapidly but highly conservatively, and without using expensive chemicals such as nucleoside triphosphates. The conservation in amplification is important since conventional PCR is known to suffer from errors introduced by mis-matched codons. Not only are such errors amplified during each cycle of PCR but more errors are created in each cycle and this creates a high background level of contamination. Cloning in a host organism can be used to detect errors and select only accurately amplified DNA.

The complementary regions of the PCR amplified DNA may be present in the target DNA but advantageously they are provided as single-stranded nucleotide extensions on the PCR primers, which extensions or 'handles' do not bind to the target DNA (as described in co-pending International patent application PCT/EP90/00454).

Preferably the PCR amplification step of the method according to the invention involves nested primers, as described in the above co-pending PCT application, and this leads to greater sensitivity in isolating and amplifying the target DNA.

Advantageously, the terminal overlapping regions are sufficiently large to provide an adequate hybridisation overlap between the PCR amplified DNA and the terminal regions of the linearised single stranded plasmid so as to form a stable cyclic product, yet still reasonably short in order to avoid unnecessary chemical synthesis, if using primer extensions. It will be clear to persons skilled in the art that the size and stability of the overlapping regions will be dependent to some degree upon the ratio of A-T to C-G base pairings since more hydrogen bonding is available in a C-G pairing. Also, it will be apparent that the smaller the overlap the more likely there will complementarity with a non-terminal region and that if the terminal regions get too large there is always the possibility that the single strand will fold back on itself and hybridise to give a hairpin or dumbbell structure. It is preferred that the overlap should be at least a ten base pair overlap, more preferably at least a twenty base pair overlap.

The term "cloning vector" as used herein includes plasmid vectors both for simple replication and for expression. A replication vector will contain an origin of replication and usually a marker e.g. an antibiotic resistance marker, to aid recognition. An expression vector will normally contain promoter and initiator sequences which must be operably connected in the same reading frame as the DNA insert if this is to be expressed correctly, as well as operator and expression control sequences and a ribosome binding site; appropriate markers e.g. antibiotic resistance markers, are usefully present. In both cases, appropriate RE sites for excision of the DNA will be desirable, especially in the replication vector.

As indicated above, the cyclic product, which is essentially single stranded apart from the two overlapping regions, may surprisingly be used after annealing to transform a host microorganism, thus avoiding the steps of second strand synthesis, and modification and ligation. Since such DNA is synthesised chemically in single stranded form, the simplified procedure of the invention lends itself to the rapid cloning of DNA so synthesised. Also, the method according to the invention is well suited to automation since no steps of precipitation, extraction, filtration, centrifugation or treatment with enzymes are required in getting the PCR-amplified DNA into a host cell.

The linearised single stranded vector may conveniently be a standard vector the terminal sequences of which comprise one or more RE sites permitting a variety of restriction endonucleases to be used to excise the DNA of interest after replication.

Most cloning vectors now in use have a common ancestry, e.g. pUC18, and include the so-called multiple cloning site including several RE sites flanked by longer regions which are also identical. In the case of pUC18, the flanking regions are part of the E. coli Lac Z gene. It may be convenient to include the multiple cloning site or at least one RE thereof with the PCR amplified DNA insert and to use the two flanking regions as the overlapping sequences in accordance with the invention. It is thus convenient to provide the DNA insert with terminal regions complementary to such standard sequences. the term "complementary" as used above means that the regions hybridise in the correct orientation to form the required cyclic product in which the overlapping 3' ends can serve as primers for synthesis of the remainder of the complete double stranded vector by the host organism.

The PCR-amplified target DNA can be cloned into different vectors provided that complementary overlap regions exist between the vector and the DNA. This is significant, for example, where it is desired to insert a gene fragment into many different vectors, such as expression vectors.

In general, to ensure adequate hybridisation and stability of the cyclic product, the overlapping regions are preferably 20 to 250 base pairs (bp) in length or even longer (e.g. 500 bp), more preferably 40 to 200 bp. However, if the overlapping regions are too long, the length of the region to be amplified may be limited in view of the fact that PCR is most effective in the region of 500 to 2,000 bp.

The hybridisation reaction is preferably effected in a 1M sodium chloride solution or an equivalent solution known in the art. (Nucleic Acid Hybridisation, B D Hames and S J Higgins, IRL Press, 1985).

In the PCR stage, the unamplified target dsDNA is first denatured and primers are annealed to both the coding and the non-coding strand. The primers are preferably those corresponding to the 5'-terminal sequences of the DNA so that on extension of the primer with a polymerase, the whole target DNA sequence of each strand will be replicated. The double stranded DNA so produced is then denatured by raising the temperature followed by rapid cooling. An excess of the primer molecules is present and these are annealed to the newly formed coding and non-coding strands. Extension using polymerase produces further double stranded DNA. The temperature cycling can be repeated many times, thereby producing a large number of copies of the DNA. Preferably, the polymerase used is one which can withstand the highest temperature of the cycle, commonly the Taq polymerase, otherwise there is a need to separate the polymerase from the nucleic acids before each heating step or replenish the polymerase after each cooling step. It is also preferred that the polymerase has a high proof-reading ability to avoid mis-matched bases and randomly introduced errors. An example of such a polymerase is vent polymerase available from New England Biolabs. Such PCR amplification provides target DNA incorporating the primers which are used. As mentioned above, nested primers may be used. In this case PCR is carried out with a first set of primers for a given number of cycles e.g. about 25. The amplified DNA is then contacted with a second pair of primers, one or both being different from the primers used earlier and being inboard of the binding sites of the first primers.

Since the method of the invention uses single stranded amplified DNA, it is advantageous for one PCR primer to carry means for immobilisation, e.g. a biotin molecule, or to be already attached to a support.

The double stranded amplified DNA may then be subjected to strand separation whereby one strand (unwanted) remains immobilised while the other is liberated into solution and can be combined with the linearised vector in accordance with the invention. Thus, such strand separation after PCR is an important preferred aspect of the invention.

However, since the linearised standard vector will hybridise only to one of the two PCR amplified DNA strands, it is also possible to liberate both strands into solution by conventional strand separation and to react these directly with the linearised standard vector. This will, however, be less efficient due to competing re-assembly of double stranded target DNA.

The PCR stage of the invention may also include a subsequent step of site-specific mutagenesis of the target DNA. In one such strategy, a standard linearised single stranded vector can be prepared by taking a plasmid in double stranded form containing two outer RE sites and two further inner RE sites inside these, each separated from the outer RE sites. The plasmid is cut at one of the inner RE sites and biotinylated followed by restriction at the other inner RE site. This provides a linearised double stranded vector which is then attached to an insoluble support coated with avidin or streptavidin. One strand of the linearised vector is thus attached to the support which the other is not and the latter can then be brought into solution by denaturation. In this example, a further plasmid contains the DNA sequence to be mutagenised flanked by sequences corresponding to the terminal regions of the single stranded linearised vector. For example the further plasmid may be the standard vector having the DNA sequence to be mutagenised inserted between the two inner RE sites. The further plasmid is subjected to at least one or two cycles of PCR amplification using primers flanking the target DNA sequence (to be mutagenised), these primers being homologous with the terminal sequences of the linearised vector. For example, the primers may correspond to the sequences between the outer and inner RE sites of the standard vector. One of the primers is provided with means for attachment to a support (e.g. a biotin group) or is already attached to the support. Chain extension provides, after a final strand separation, the target DNA in single stranded form linked at one end to a support. Hybridisation to a further primer at the 3'-end to initiate chain extension and a mutagenesis primer incorporating the desired mutation, permits synthesis, in the presence of a polymerase, of a DNA strand incorporating the mutation and flanked by terminal sequences complementary to those of the linearised vector. Strand separation, e.g. by treatment with alkali, liberates the mutagenised strand into solution while the template is immobilised and thus readily separated. The mutagenised ss DNA may then be contacted with the linearised vector and annealed to give a cyclic product in accordance with the invention.

The target DNA may be cDNA produced by reverse transcription from mRNA, and the method according to the invention therefore provides a way of direct cloning cDNA. For example, mRNA may be immobilized on a solid support bearing poly dT which hybridises to the poly A tails of the mRNA.

Preferably, the connection of the poly dT to the solid support includes a suitable RE site. Reverse transcription can then be effected advantageously using the poly dT as a primer. The mRNA is then removed leaving the newly synthesised single-stranded cDNA attached to the solid support.

The single-stranded cDNA may be made double-stranded by use of a suitable polymerase, e.g. T4 polymerase, and the free end of the cDNA may have attached thereto a linker using a suitable ligase. In this case the linker and the sequence proximate the solid support are, advantageously, complementary to the terminal regions of the plasmid vector. The double-stranded cDNA can then be subjected to PCR in accordance with the invention; the PCR primers corresponding to the linker sequence and the sequence proximate the solid support. Alternatively, the linker and/or sequence proximate the solid support may not be complementary with the terminal regions of the vector in which case such complementary regions can be provided by using PCR primers with handles.

Instead of forming double-stranded cDNA as mentioned above, it is possible to use a terminal transferase to add several molecules of one type of nucleotide to the 3' end of the single-stranded cDNA to form a tail, for example a dG tail. Thus the single-stranded cDNA comprises a 5' poly dT sequence near the support (which sequence hybridised to the poly A tail of the mRNA) and a 3' tail, for example poly dG. PCR can now be initiated using poly dT and poly dC primers. The linearised single-stranded vector preferably has complementary terminal poly dA and poly dC regions in order to form the cyclic product with the PCR amplified single-stranded cDNA. As mentioned above, it is of course possible to use primers in the PCR amplification which comprise either poly dT or poly dC and appropriate handles to form the overlap with complementary regions of the vector.

The method according to the invention in combination with direct solid phase DNA sequencing can be used to analyse target DNA, for example alleles of a locus e.g. the human apolipoprotein E locus and may thus be used for diagnosis of physiological conditions. Such analysis may include sequencing, as will be exemplified below. Moreover, the method according to the invention can be used in a diagnostic method, for example testing for the presence of a certain allele. For example, the cloning may be followed by direct sequencing to separate and identify both alleles in a heterozygote. Such direct clinical sequencing to detect polymorphism has the advantages that non-expected nucleotide changes in close proximity to the allele analysed will be detected and that flanking sequences can be used as positive controls in order to verify that the non-expected exchange was not due to the earlier PCR amplification.

Clearly, in such methods as above where one is investigating genomic DNA, overlapping terminal regions are provided by the primers during amplification; there is no need to provide specific terminal RE sites to allow incorporation of the target DNA into a vector (as required in conventional cloning and amplification protocols). However, it is preferably that RE sites are incorporated adjacent the target DNA since such RE sites will allow for subsequent excision of the cloned target DNA from the vector. RE sites can be conveniently provided in the overlapping terminal regions provided by the primers during amplification. If, for example, the vector includes a multiple cloning site having many RE sites, one site can be selected for restriction and the overlapping regions of the primers will then be complementary to the terminal regions either side of the selected restricted site.

It should be noted that it is preferable to remove any excess primer remaining after PCR amplification since otherwise it will compete with the terminal regions of the plasmid to hybridise with the amplified DNA.

It will be appreciated that in any of the above systems, the biotin/avidin or streptavin affinity coupling may be replaced by other such coupling using a relatively small molecule and binding partner, e.g. an antigen and antibody therefor, or covalent coupling as indicated below.

An advantage in PCR strategies involving immobilised site-specific mutagenesis is that the template is readily removed completely from the synthesised DNA, thus avoiding contamination with unmutated DNA.

As mentioned earlier, it may be convenient in some of the above PCR strategies to use PCR primers having 'handles' of DNA not hybridising in the first cycle of the PCR amplification, such handles corresponding to the terminal regions of the standard vector while the hybridising regions of the primers correspond to regions of a source of target DNA e.g. genomic DNA. This applies equally to PCR amplification with or without mutagenesis.

The insoluble support, where used, may take a variety of forms, for example microtitre wells, filters made from materials such as cellulose or nylon, or particles including, for example, sephadex or sepharose beads or polystyrene latex particles. It is a preferred feature of the invention to use magnetic particles which may be aggregated onto a surface and then be readily redispersed for a subsequent treatment step, e.g. by physical agitation.

Probe and primer oligonucleotides may be prepared by using any of the commercially available DNA synthesis devices, e.g. those available from Applied Biosystems, Inc. (850-T Lincoln Center Drive, Foster City, Calif. 94404).

Some aspects of the process of the invention are in part disclosed in our International Patent Application No. PCT/EP89/01417 the contents of which are incorporated herein by reference.

The invention also includes kits for carrying out the cloning procedure of the invention comprising one or more of the following:

a) a standard linearised vector in single stranded or double stranded form the said double stranded form immobilised by one end of one strand thereof.

b) an insoluble support carrying one member of a pair of binding partners.

c) nucleotides carrying the other member of said pair of binding partners.

d) a polymerase.

e) 2 PCR primers corresponding to the terminal regions of said standard vector one of which is adapted to bind to said support.

f) a thermostable polymerase.

g) an alkaline solution for strand separation.

The invention will now be described by way of non-limiting examples with reference to the drawings in which.

EXAMPLE 1

In vitro mutagenesis on latex particles.

Figure 1:
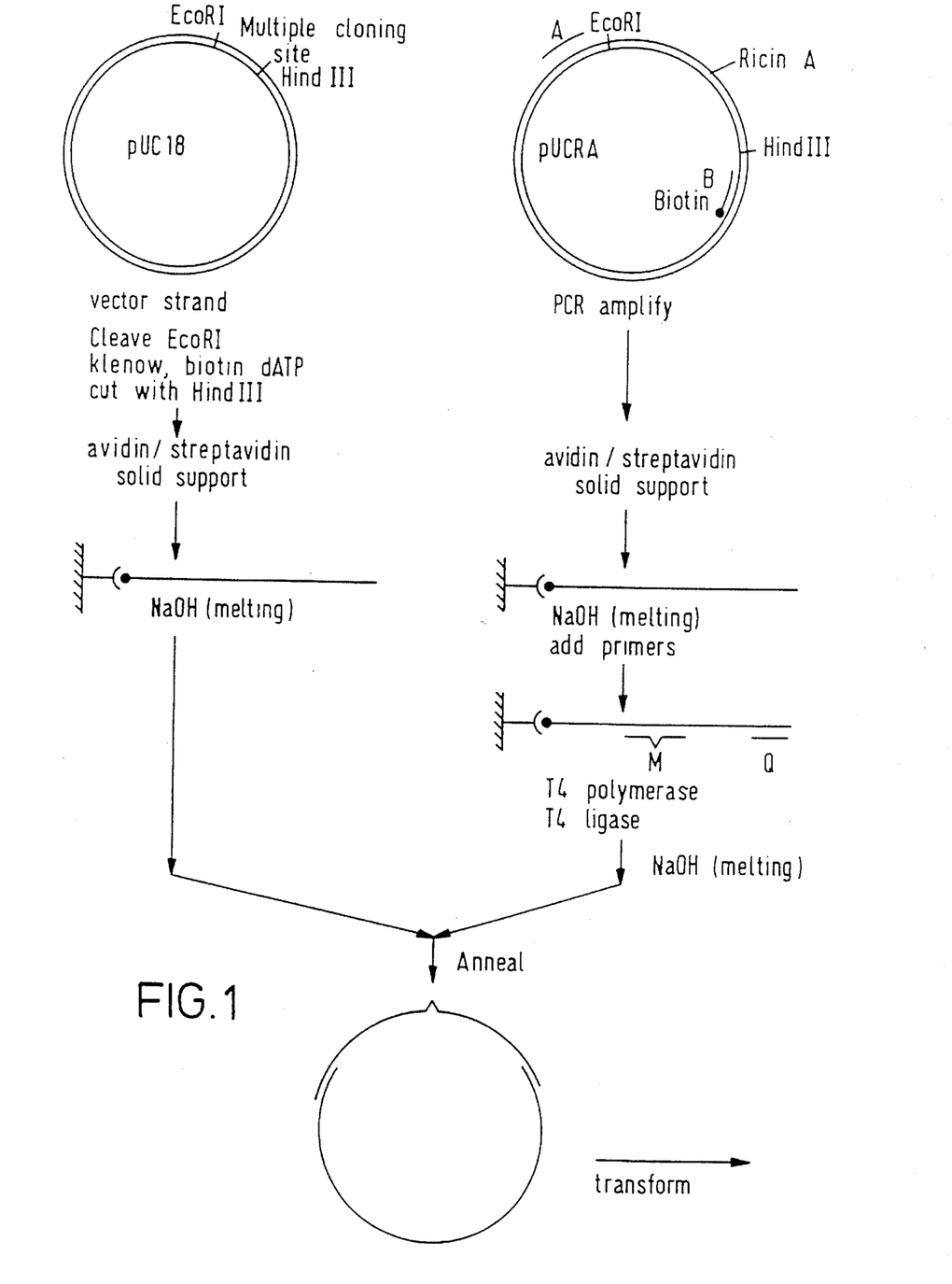
FIG. 1 shows a protocol for site-specific mutagenesis using the method according to the invention.

The protocol shown in FIG. 1 was used (a) To yield the ss vector template 10 μg of pUC18 were digested with EcoRI in a total volume of 50 μl. The 5' protruding ends were filled in using Klenow polymerase (5 U) and 2 μl Biotin-7-dATP (BRL), 7.5 μl of a buffer containing 100 mM Tris-HCl (pH 7.5), 100 mM $MgCl_2$ and 1M NaCl. The volume was adjusted to 75 μl with water. The reaction was performed at room temperature during one hour and after that purified using a sephadex G50 spin column. The purified biotinylated linearized vector was cut with HindIII. The reaction containing the biotinylated double stranded DNA was mixed with previously washed Pandex avidin particles, (Baxter Healthcare Corp., Mundelin, Ill., USA).

To yield the ss vector template the immobilized doublestranded DNA was converted into singlestranded form by melting off the non attached strand by incubation at 37° C. with 20 μl 0.15M NaOH for 10 minutes. The pH of the supernatant was immediately adjusted with 1.5 μl HAc (1.7M) and 2.2 μl 10×TE (100 mM tris pH 7.5, 10 mM EDTA).

(b) To yield the mutagenesis template, the inserted fragment from pUCRA was PCR amplified using 10 pmol of primer A (SEQ ID No: 1) TGC-TTC-CGG-CTC-GTA-TGT-TGT-GTG3' and biotinylated primer B (SEQ ID No.: 2) Biotin-AAA-GGG-CGA-TGT-GCT-GCA-AGG-CGA3' in 25 μl PCR reaction mixture as recommended by Perkin Elmer and amplified for 20 cycles. After PCR amplification, Pandex avidin particles were added to immobilize the amplified insert with flanking vector sequences.

(c) To yield template for in vitro mutagenesis the immobilized PCR amplified fragment was made single stranded with 0.15M NaOH for 10 minutes at room temperature. 10 pmol were added of each primer Q (SEQ ID No.: 3) 5'CGG-CTC-GTA-TGT-GTG-GAA-TTG and mutagenesis primer M (SEQ ID No.: 4) 5'CC-AAT-GCA-TAT-GTG-GTC-GGC-TAC-GCT-GGA-AAT-AGC-GCA-TAT-TTC3' (the original sequence (SEQ ID No. 5) was: CCAAT GCA-TAT-GTG-GTC-GGC-TAC CGT GCT GGA AAT AGC-GCA) were annealed to the template immobilized on the Pandex avidin particles in a solution containing 10 mM Tris-HCl (pH- 7.5), 10 mM $MgCl_2$, 100 μg/ml BSA and 100 mM NaCl. The mixture was incubated at 65° C. for a few minutes and allowed to cool to room temperature.

(d) Extension was performed by adding 1 μl BSA (100 μg/ml), 6 μl polymerase mix (100 mM Tris-HCl pH 8.8, 10 mM DDT), 50 mM $MgCl_2$ and 5 mM ATP), 6 μl chase (10 Mm each of dNTP) and 3.5 U $T_4$ DNA polymerase. 1 unit of $T_4$DNA ligase was added to the beads containing the insert strand.

The volume was adjusted to 30 μl with water. The mixture was incubated at RT for 20 minutes followed by incubation on a roller mixer at 37° during two hours.

(e) After extension the beads were washed once with TE. The newly synthesized strands were melted off by incubation with 20 μl 0.15M NaOH at 37° during 10 minutes. The pH of the supernatant was immediately adjusted with 1.5 μl HAc (1.7M) and 2.2 μl 2×TE.

The two supernatants, the single stranded vector and the newly mutated insert with flanking vector sequences were mixed and incubated at 70° C. for 10 minutes and allowed to cool to RT.

After annealing of the two strands the $CaCl_2$ concentration was adjusted to 0.1M and E. coli DH5α was transformed with DNA and spread on TRAB plates containing IPTG and X-Gal.

EXAMPLE 2

Direct cloning of the human genomic apolipoprotein E gene using magnetic separation of single stranded DNA.

Materials and Methods

Clinical samples

Leukocytic DNA from venous blood samples from patients having the genotype E2/4 was kindly provided by A.-C. Syvänen and K. Aalta Setälä (1) (Orion Corporation, Helsinki, Finland).

Preparation of the primers

Four PCR primers (denoted RIT113, 114, 123 and 125) were synthesized on an Applied Biosystems 381A DNA synthesizer. 5'-amino modified oligunucleotides (RIT123) were synthesized using the reagent Aminolink 2 (ABI, USA). A biotin residue was attached to the amino group using the reagent Biotin-X-NHS ester as described by the manufacturer (Clontec, USA) and the biotinylated oligonucleotide was purified by reverse phase HPLC. The fluorescent M13 universal sequencing primer was purchased from Pharmacia LKB Biotechnology, Sweden. The two primers RIT 123 and RIT 125 contained a 5'sequence (22 nucleotides) complementary to the pUC vector.

Polymerase chain reaction

The DNA (100 ng per sample) was amplified with the RIT113 and RIT114 primers at final concentration of 1 μM. The PCR was carried out in 100 μl of a solution consisting of 0.2 mM each of the dNTP:s 20 mM Tris-HCl, pH 8.8, 15 mM $(NH)_2SO_4$ 1.5 mM $MgCl_2$ 0.1% Tween 20, 0.1 mg/ml gelatin and 2.5 units of Taq polymerase (United States Biochemical Corp, USA) in a thermal cycler (Perkin-Elmer, USA) for 25 cycles of 1 min. at 96° C. and 2 min. at 65° C. For amplification with a second pair or primers a small aliquot (3 μl of 1:100 μl dilution) of the PCR product amplified with the primers RIT113 and RIT114 was transferred to a second PCR. This was carried out at the conditions described above using the biotinylated primer RIT123 and the primer RIT125 at 0.1 μM concentration.

Immobilization on magnetic beads

Magnetic beads containing covalently attached Streptavidin. Dynabeads® M280 Streptavidin, were obtained from Dynal (N-0212 Oslo 2, Norway). A neodynium-ironboron permanent magnet MPC-E, (Dynal, Norway) was used to sediment the beads in the tubes during supernatant removal and washing procedures. The PCR mixture was added to 300 μg of Dynabeads® M280 Streptavidin previously washed with TE buffer (10 mM Tris pH 7.5, 1 mM EDTA) containing 1M NaCl, and incubated 15 min. at room temperature.

Preparation of single stranded vector

A total of 5 μg of pUC18 (Pharmacia LKB Biotechnology, Sweden) was digested with EcoRI, phenol extracted followed by desalting with a sephadex G50 spin column. Biotin-7-dATP (BRL, USA) was introduced by Klenow polymerase. After heat inactivating and desalting it was digested with HindIII and immobilized on 1 mg of Dynabeads® M 280 Streptavidin. Strands were separated using 40 μl 0.12M NaOH. The supernatant was neutralized by adding 3.7 μl 1.7M HAc and 4.4 μl 10×TE buffer pH 7.5. The concentration was estimated using agarose gel electrophoresis.

Direct cloning

The PCR amplified apoE gene region containing ends complementary to the single stranded vector was immobilized on magnetic beads. The strands were separated using 40 μl 0.12M NaOH. The supernatant was neutralized by adding 3.7 μl 1.7M HAc and 4.4 μl 10×TE buffer PH 7.5 and concentration estimated. 100 ng single stranded vector was mixed with an equal amount of single stranded genomic amplified DNA in a total of 5 μl. Transformation of competent E. coli DH5α cells (BRL.USA) was performed according to the manufacturer's direction.

Sequencing reactions

The immobilized dsDNA was washed with 50 μl TE buffer and then incubated with 10 μl 0.1M NaOH for 15 min. at room temperature. The supernatant was removed and the beads containing the immobilized single stranded DNA were washed with 50 μl 0.15M NaOH and 3 times with 50 μl TE buffer. The volume was adjusted to 13 μl with $H_2O$.

All sequencing reactions were performed with reagents from the AutoRead sequencing kit (Pharmacia LKB Biotechnology, Sweden). 2 μl (1 pmol) of a fluorescent labelled universal sequencing primer was added to each Eppendorf tube together with 2 μl of annealing buffer. The annealing mixtures were incubated at 65° C. for 15 min. and allowed to cool to room temprature for 15 min. 1 μl of a MID solution (Manganese, Isocitrate and DTT) was added to each annealing mixture together with 2 μl T7 polymerase (1.5 units/μl) and 2.5 μl of respectively A,C,G,T sequencing mixture (containing $c^7dGTP$ instead of dGTP) were prewarmed at 37° C. for 1 min. using a microtest plate (Sarstedt, West Germany) before 4.5 μl of the annealing mixture was added to each sequencing mixture and incubated for 5 min. at 37° C. 5 μl of deionized formamide containing Blue Dextran was added to stop the reactions. the microtest plate was heated at 80° C. for 2 min. and 5 μl was loaded on a 6% sequencing gel run on an automatic sequencing apparatus with detection of fluorescent bands during electrophoresis (A.L.F, Pharmacia LKB Biotechnology, Sweden).

RESULTS

The principle for solid phase cloning

Figure 2:
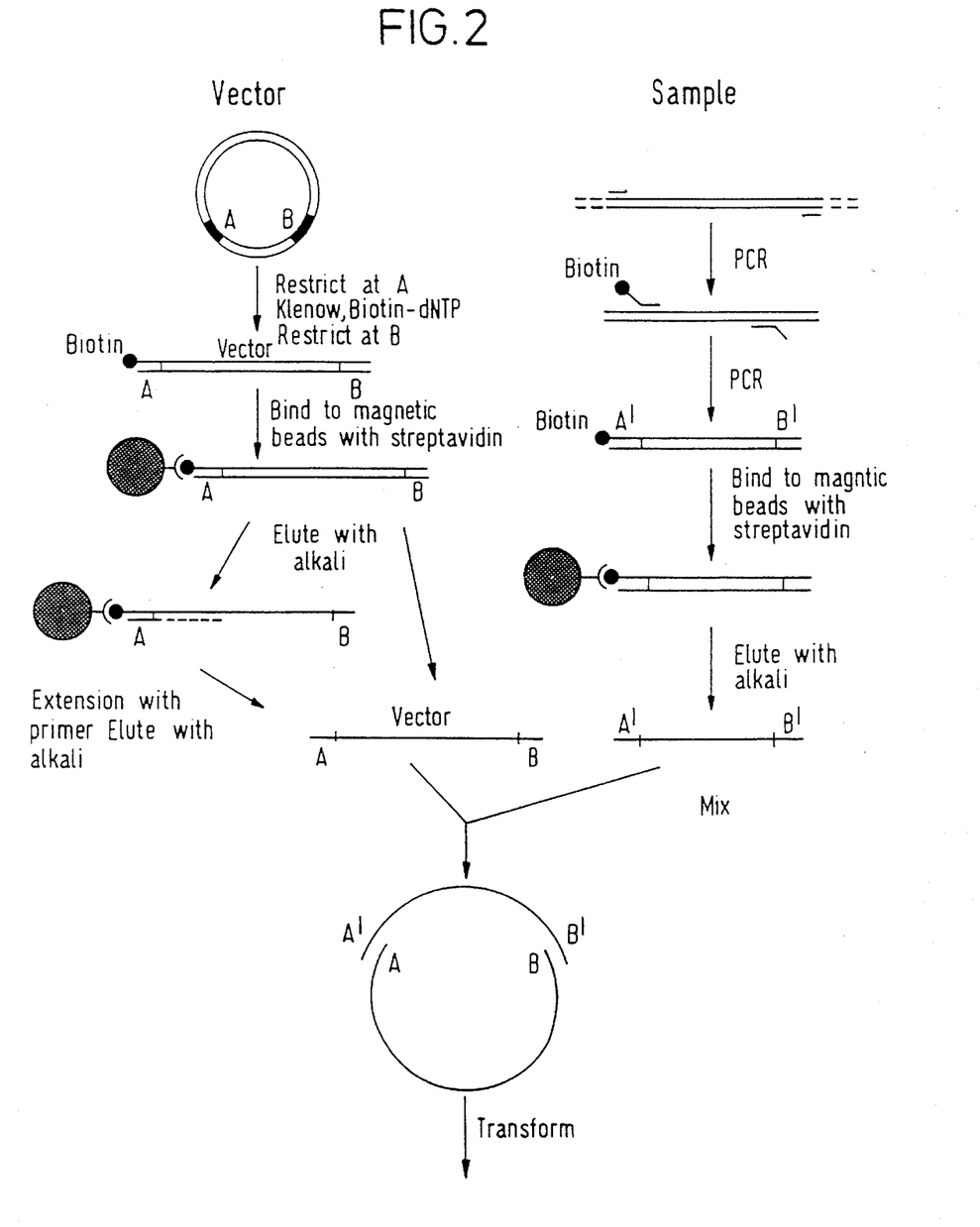
FIG. 2 shows a protocol for amplification of genomic DNA using the method according to the invention.

A basic concept for cloning using a solid phase approach is shown in FIG. 2. A single stranded vector fragment is provided by selectively incorporating biotin into one of the strands of the vector DNA. This is achieved by restriction and fill-in using a biotin-dNTP and DNA polymerase. The double stranded DNA is bound to magnetic beads containing streptavidin and the single stranded vector is simply eluted with alkali. If more single stranded vector fragment is needed, a run-off extension reaction with DNA polymerase can be carried out, one or several times, and the extended fragment is again eluted with alkali and collected. This yields a well defined single stranded vector with flanking sequences represented by the A and B region (FIG. 2).

Alternatively, the vector fragment can also be prepared by the apparently simple PCR procedure using specific vector primers. However, caution must be taken as PCR of large fragments might create random polymerase errors into the vector part which is not easy to control. In addition, PCR of larger fragments (>3 Kb) is not yet straight forward in terms of reproducibility and yield.

The "insert" DNA to be cloned is obtained by PCR, using specific primers with handles consisting of the vector regions A and B, respectively (FIG. 2). For genomic DNA specific primers need to be synthesized, while for gene fragments inserted into vectors it is possible to use general PCR primers designed for the solid phase cloning. In both cases, one of the primers contains a biotin in the 5' end, which allows the in vitro amplified material to be captured by Streptavidin coated magnetic beads. A single stranded insert fragment with flanking regions (A' and B') complementary to the vector fragment can subsequently be eluted with alkali. The two single stranded fragments can then be mixed to form a gap-duplex molecule (FIG. 2) and transformed directly in E. coli. The method allows cloning of any fragment, from any origin (chromosomal DNA, plasmid DNA etc.) independent on restriction sites. No restriction enzymes and ligase are needed and very high yield of recombinants is expected since the vector and insert alone should not give transformants.

Design of primers for the human apolipoprotein E gene

The solid phase approach was tested by analysing the chromosomal gene fragments of the apolipoprotein E (ApoE) gene. Mature ApoE is a 299 amino acid protein which plays an important role in the lipoprotein metabolism (2). In humans, three major apoE isoproteins exist (3), apoE2, E3 and E4, encoded by the three different co-dominant alleles (E2, E3 and E4). Besides apoE2 ($cys_{112}$, $cys_{158}$), E3 ($cys_{112}$, $arg_{158}$) and E4 ($arg_{112}$, $arg_{158}$), several rare, independent apoE isoproteins have recently been described in this region (4). Sequencing of individual chromosomes is therefore of importsance to establish the structure of the alleles in this region on both chromosomes.

Figure 3:
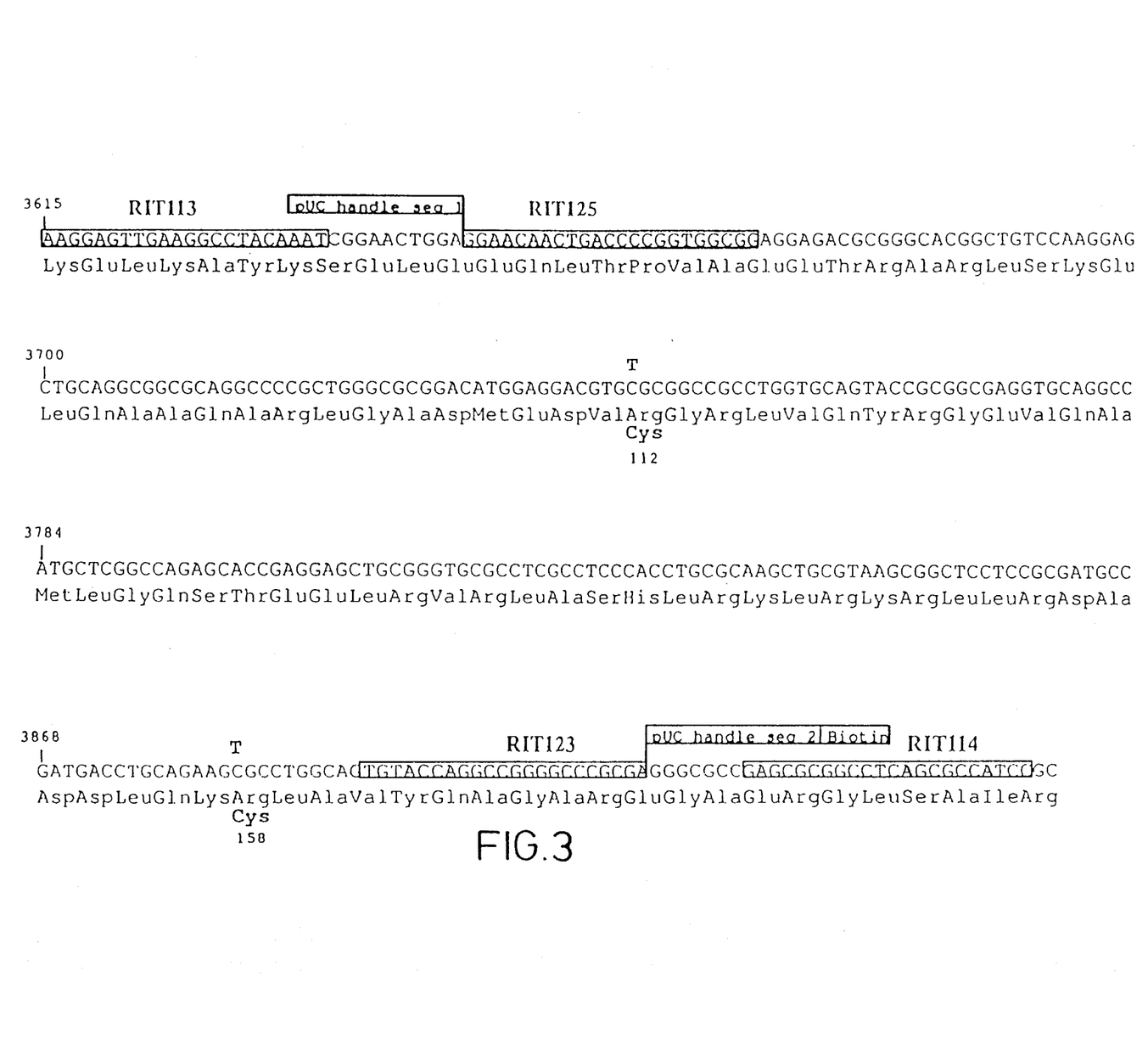
FIG. 3 (SEQ ID Nos. 6 and 7) shows a region of a human lipoprotein E gene together with primers.

The polymorphic region of apoE is due to single base substitutions at two loci, a C/T nucleotide change at codon 112 and a similar C/T nucleotide change at codon 158. Both mutations give rise to an arginine to cysteine replacement (FIG. 3). To test the solid phase cloning protocol (FIG. 2), a nested primer approach was followed with a pair of outer primers and another pair of inner primers (FIG. 3) used for the cloning (RIT 123 and RIT 125) and thus containing handle sequences complementary to the pUC vector. The downstream primer (RIT123) contains a 5'-biotin to allow capture of the amplified chromosomal DNA.

Direct solid phase cloning of the chromosomal apoE gene

Blood samples from several human patients were prepared (1) and used for a two step (25 cycles each) PCR procedure using the outer primers (RIT 113 and RIT 114) and the inner primers (RIT123 and RIT 125). For details see Materials and Methods. Analysis by agarose electrophoresis showed a band of the expected 290 bp for all samples (data not shown).

The PCR product for one of the patients was bound to the magnetic beads and the single stranded insert was eluted with alkali and neutralized. The vector fragment from pUC18 was prepared by restriction with EcoRI, followed by a fill-in reaction with biotin-dATP and by restriction with HindIII. After binding to magnetic beads, the single stranded vector was eluted with alkali and neutralized.

The single stranded vector and the eluted single stranded PCR fragment were mixed and used directly to transform competent E.coli cells. Several hundred colonies were obtained, while transformation with the vector or the insert alone, gave a few or none colonies, respectively (data not shown). Restriction mapping of purified plasmids from 20 colonies showed that 19 recombinants had plasmid with an insert of the correct size (data not shown).

Sequencing of positive clones

Figure 4A:
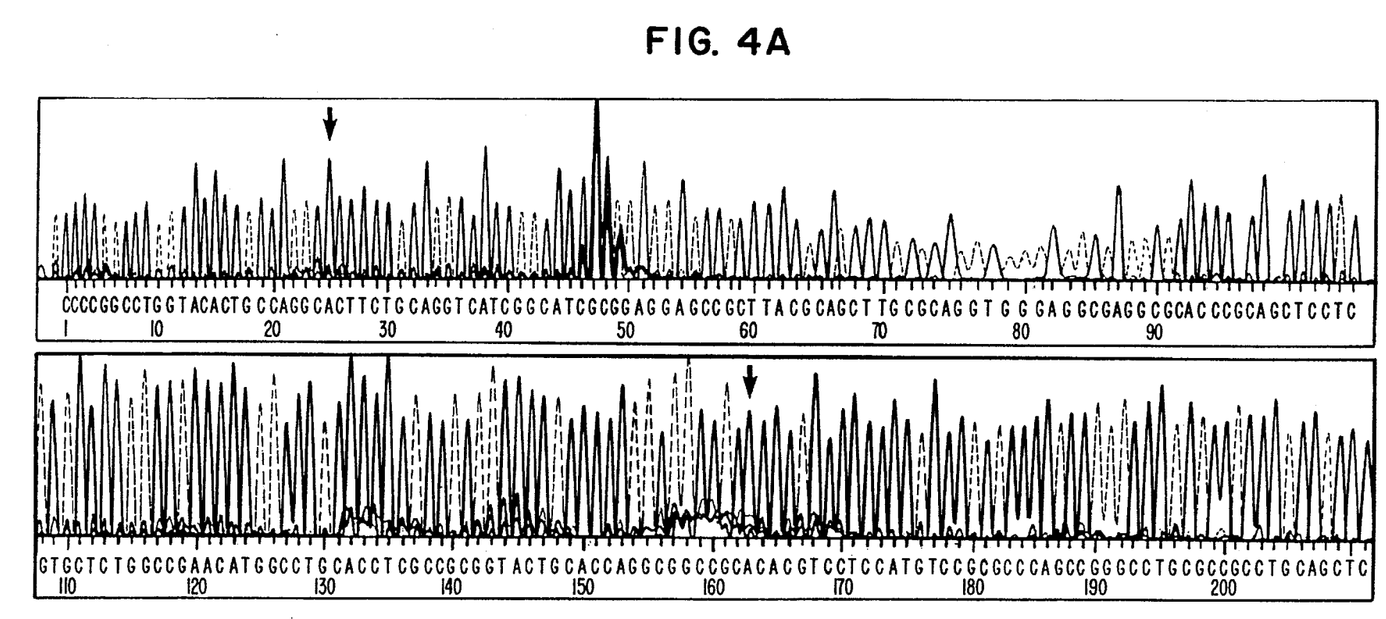
FIG. 4A and B show sequencing printouts for two clones.
Figure 4B:
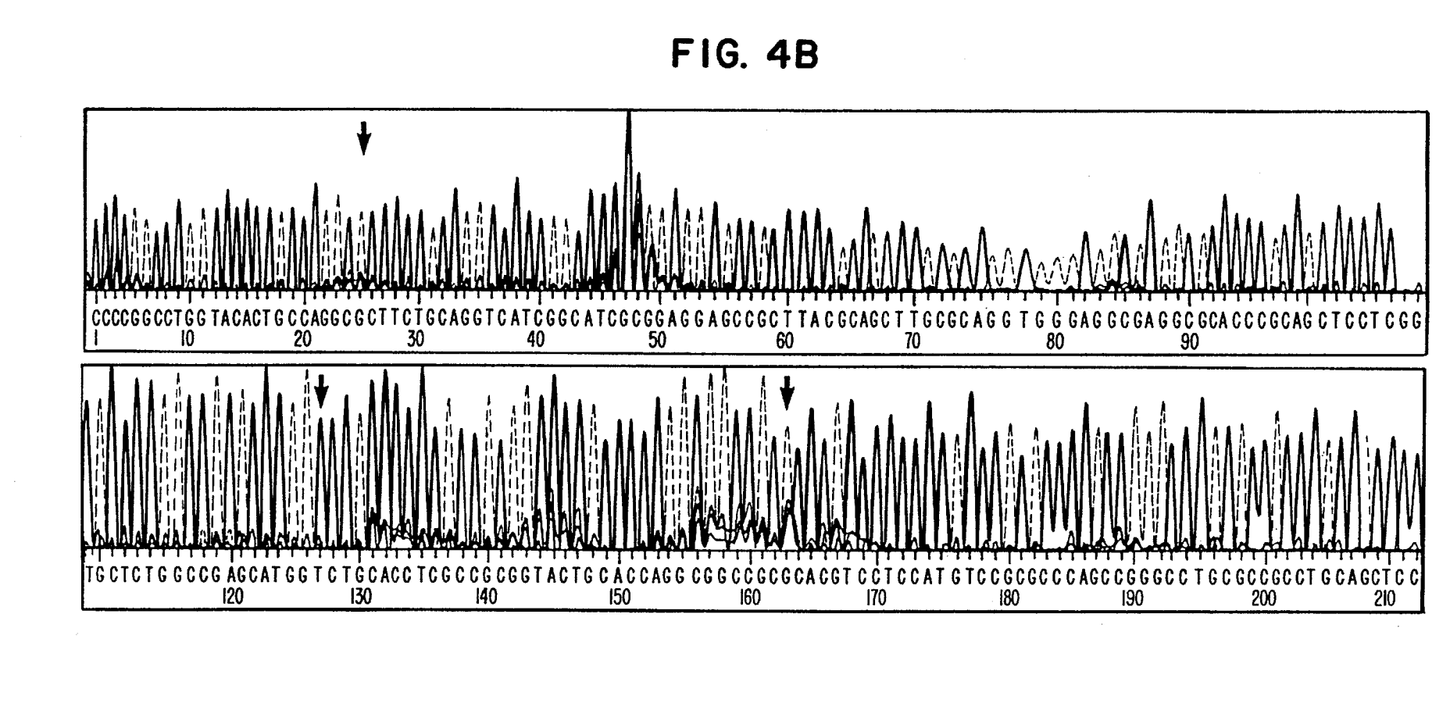

Six of the colonies from the mixing experiment were sequenced directly by the solid phase method (5). Examples of two of the samples are shown in FIG. 4. The sequence data show that one of the clones (FIG. 4A) has a G/G in the polymorphic positions (arrows) corresponding to a C/C loci. In contrast the other clone has an A/A (FIG. 4B) in these positions, suggesting a T/T genotype. Of the six clones sequences, four were of the T-T genotype, while two were of the C-C type. Clearly, the patient is a heterozygote E2/4 with an $arg_{112}$, $arg_{158}$ coded by one of the chromosomes, while the other chromosome codes for an apoE protein with a $cys_{112}$, $cys_{158}$. An interesting observation is that four of the six clones sequenced showed different unique sequences outside the allelic codons, such as the T at position 127 in FIG. 4B. These nucleotide changes correspond to polymerase errors obtained during the repetitive PCR procedure. Two of the clones, such as the one showed in FIG. 4A, contained a sequence without any random errors.

DISCUSSION

We have for the first time shown that magnetic separation of DNA can be used for efficient assembly of recombinant DNA molecules. Here, individual human chromosomal gene fragments were directly cloned by PCR simply by using a 22 basepair primer "handle" complementary to the ends of the linear vector fragment during the PCR. The cloning step is simple, rapid and involves no ligation and restriction enzyme reactions. The yield of specific chromosomal clones was approximately 90% without using any positive selection or any special host strain.

The fragment produced can be cloned into different vectors provided that complementary overlap regions exist between the vector and the insert. This allows for the use of a battery of prepared single stranded vectors, in which the insert is directly cloned simply by mixing and transforming. This procedure is well suited for automation since no precipitations, extractions, filtrations or centrifugations are needed and no enzymatic steps are performed. Thus both manual, semi-automated procedures can be envisioned. This is significant for large scale projects, where it is desired to insert a gene fragment into many different vectors, such as various expression vectors.

The cloning protocol (FIG. 2) has the advantage that the same principal result can be accomplished both with or without using PCR to prepare the linearised vector. This is important since accumulated polymerase errors are a major concern when ever PCR products are cloned (6), which makes it strongly desired to sequence the cloned material. For large sized fragments such as cloning and expression vectors, this is difficult and time consuming. Therefore, solid phase cloning protocols that do not depend on PCR produced vector are attractive. In this Example, the vector was produced by the restriction-fill-in procedure to avoid PCR amplification of larger sized fragments while the cloned chromosomal ApoE gene was obtained by PCR.

As expected, the cloned material has considerable amounts of randomly introduced errors (FIG. 4). As the error frequency of Taq polymerase is approximately $10^{-4}$ (2) and the PCR was carried out for 2×25 cycles, the theoretical error frequency for each nucleotide is roughly 1 out of 200 (10.000/50). This background (less than 1 per cent) is obviously not observed when a direct genomic sequencing is carried out. Even if only one template molecule is present in the original sample and an error is introduced in the first cycle, the correct signal at that position is theoretically 75% and can possibly be discriminated from background.

In contrast, when the same material is cloned, for example in *E. coli*, the random errors become prominent readily detectable. For a fragment of the size of 200 basepairs (as the human apoE gene described here) and error frequency of 1/200 means that most fragments will contain an introduced error. The results of the cloning confirm this as 4 out of 6 cloned fragments contained random errors. The high frequency of introduced errors detected in the fragments after cloning can of course be limited by performing less PCR cycles or to avoid the nested primer approach. It might also be possible to use a less error prone polymerase. However, as long as relatively short fragments are cloned and a straight forward sequencing of several clones can be performed, it should be possible to find a clone with a correct sequence by a small scale screening. Note, that the correct genomic sequence can be determined and defined by the direct genomic solid phase sequencing (5).

Interestingly, the cloning procedure followed by direct sequencing using an automated electrophoresis instrument can be used to separate and identify both alleles in a hetrozygote. Thus, a diagnostic evaluation may be performed in an automated manner, which is in contrast to most polymorphic analysis based on hybridization (7). A direct clinical sequencing approach for diagnosis of polymorphism has the additional advantages that non-expected nucleotide changes in close proximity to the allele analyzed will be discovered and that the flanking sequences can be used as positive control to show that the PCR reaction has been successful and specific.

In conclusion, the direct cloning procedure according to the invention was able to isolate and sequence individual human chromosomal apoE gene fragments. Thus, the relationship between two separated alleles could be resolved. The results demonstrate the selectivity and efficiency obtained by the solid phase approach as all the recombinants sequenced had the desired chromosomal gene fragment. The cloning using magnetic separation is thus a highly efficient, rapid and simple tool to obtain recombinant molecules, although caution must be taken to minimize the effect of random errors introduced during the PCR by the Taq polymerase. This method and similar procedures can facilitate considerably the assembly of cloned genes in molecular biology and biotechnology.

References

1. Syvänen, A. -C., K. Aalto-Setälä, K. Kontula and H. S öderlund. 1989. Direct sequencing of affinity-captured human DNA: application to the detection of apolipoprotein E polymorphism. FEBS Lett. 258:71–74.
2. Mahley, R. W. 1988 Apolipoprotein E: Cholesterol Transport Protein with Expanding Role in Cell Biology. Science 240:622–630.
3. Zannis, V. I., P. W. Just and J. L. Breslow. 1981. Human apoliprotein E isoprotein subclasses are genetically determined. Am J. Hum. Gent 65 232–236.
4. Paik, Y. -K., D. J. Chang, C. A. Reardon, G. E. Davies, R. W. Mahley and J. M. Taylor, 1985. Nucleotide sequence and structure of the human apolipoprotein E gene. Proc. Natl. Acad. Sci. USA 82:3345–3449.
5. Hultman, T., S. Ståhl, E. Hornes and M. Uhlén. 1989. Direct solid phase sequencing of genomic and plasmid DNA using magnetic beads and solid support. Nucleic Acids Res. 17:4937–4946.

6. Tindall, K. R. and T. A. Kunkel. 1988 Fidelity of DNA synthesis by the Thermus aquaticus DNA polymerase, Biochemistry 27:6008–6013.

7. Caskey, C. T. 1987, Disease Diagnosis by Recominant DNA Methods. Science 236:1223–1229.

---

We claim:

1. A method of cloning a target DNA, wherein
   (a) said target DNA is amplified by PCR to obtain single-stranded amplified target DNA,
   (b) the single-stranded, amplified target DNA is contacted with a single-stranded, linear vector DNA having terminal regions which are complementary to respective terminal regions of said amplified target DNA, wherein said complementary terminal regions overlap and hybridize to form a cyclic DNA product comprising single-stranded target DNA, single-stranded vector DNA, and two double-stranded regions formed by hybridization of said overlapping complementary terminal regions of the single stranded vector and the single stranded amplified target DNA, wherein said double-stranded regions are separated from each other by a region of single-stranded target DNA, and wherein said cyclic DNA product is essentially single-stranded apart from said double-stranded complementary regions,
   (c) said cyclic DNA product is introduced into a host organism, and
   (d) said cyclic DNA product is cloned by replication of said host organism.

2. A method of cloning target DNA as claimed in claim 1, wherein the PCR is two-stage and uses nested primers, each primer of the second stage being complementary to a sequence of the target DNA between the sites complementary to the first stage primers.

3. A method as claimed in claim 2, wherein said second stage primers comprise single-stranded 5' nucleotide extensions which form terminal regions in one strand of the amplified target DNA that are complementary to the terminal regions of said single stranded vector.

4. A method as claimed in claim 1, wherein each of said double-stranded regions of the cyclic DNA product comprises at least one restriction site.

5. A method as claimed in claim 1, wherein PCR is effected using two primers, one of which carries means for immobilization or is already immobilized.

6. A method as claimed claim 1, wherein site-specific mutagenesis is effected between the steps of PCR amplification and formation of the cyclic DNA product.

7. A method as claimed in claim 6, wherein amplified target DNA is immobilized prior to said site-specific mutagenesis.

8. A method as claimed in claim 1, further comprising the steps of recovering cloned DNA from said host organism having introduced therein said cyclic DNA and then determining in said cloned DNA a sequence in said target DNA.

9. A method as claimed in claim 1, wherein the single stranded linear vector DNA is produced by a method comprising immobilizing only one end of only one strand of a double-stranded linear vector DNA and separating the non-immobilized strand from the immobilized strand wherein said non-immobilized strand is said single stranded linear vector.

10. A kit for cloning target DNA comprising:
    (a) a linear vector
       (i) in single stranded form having terminal regions that are complementary to respective terminal regions of a target DNA, whereby said complementary terminal regions overlap and hybridize to form a cyclic DNA product comprising single stranded target DNA, single stranded vector DNA, and two double stranded DNA regions wherein said double stranded regions are separated from each other by a region of single stranded target DNA, and wherein said cyclic DNA product is essentially single stranded apart from said double stranded complementary regions; or
       (ii) in double stranded form and immobilized by one end of one strand thereof, wherein the single stranded linear vector is produced by separation of the non-immobilized strand from the immobilized strand;
    (b) a polymerase;
    (c) two PCR primers for amplification of the target DNA, wherein said PCR primers correspond to the terminal regions of said vector;
    (d) nucleoside triphosphates.

11. A kit as claimed in claim 10 additionally comprising means for sequencing target DNA including either labelled primer or labelled nucleoside triphosphates.

12. A kit as claimed in claim 10 additionally comprising means for site-specific mutagenesis including:
    (a) a site specific mutagenic amplification primer;
    (b) a second polymerase; and
    (c) a ligase.

13. A method of cloning a target DNA according to claim 1, wherein said overlapping complementary regions are 20–250 base pairs in length.

14. A method of cloning a target DNA according to claim 1, wherein said overlapping complementary regions are about 20 base pairs in length.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( i i ) MOLECULE TYPE: Other nucleic acid;
        ( A ) DESCRIPTION: Synthetic DNA oligonucleotide     ( x i ) SEQUENCE DESCRIPTION: SEQ ID NO:1:

```
TGCTTCCGGC   TCGTATGTTG   TGTG                                           24
```

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( i i ) MOLECULE TYPE: Other nucleic acid;
        ( A ) DESCRIPTION: Synthetic DNA oligonucleotide     ( x i ) SEQUENCE DESCRIPTION: SEQ ID NO:2:

```
AAAGGGGAT    GTGCTGCAAG   GCGA                                           24
```

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: Other nucleic acid;
        ( A ) DESCRIPTION: Synthetic DNA oligonucleotide     ( x i ) SEQUENCE DESCRIPTION: SEQ ID NO:3:

```
CGGCTCGTAT   GTGTGGAATT   G                                              21
```

( 2 ) INFORMATION FOR SEQ ID NO:4:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear     ( i i ) MOLECULE TYPE: Other nucleic acid;
        ( A ) DESCRIPTION: Synthetic DNA oligonucleotide     ( x i ) SEQUENCE DESCRIPTION: SEQ ID NO:4:

```
CCAATGCATA   TGTGGTCGGC   TACGCTGGAA   ATAGCGCATA   TTTC                 44
```

( 2 ) INFORMATION FOR SEQ ID NO:5:

( i ) SEQUENCE CHARACTERISTICS:
        ( A ) LENGTH: 41 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:5:

CCAATGCATA TGTGGTCGGC TACCGTGCTG GAAATAGCGC A     41

(2) INFORMATION FOR SEQ ID NO:6:

(i) SEQUENCE CHARACTERISTICS:
        (A) LENGTH: 330 base pairs
        (B) TYPE: nucleic acid
        (C) STRANDEDNESS: single
        (D) TOPOLOGY: linear     (ii) MOLECULE TYPE: DNA (genomic)

(vi) ORIGINAL SOURCE:
        (A) ORGANISM: HUMAN LIPOPROTEIN E GENE     (ix) FEATURE:
        (A) NAME/KEY: CDS
        (B) LOCATION: 1..330

(xi) SEQUENCE DESCRIPTION: SEQ ID NO:6:

```
AAG GAG TTG AAG GCC TAC AAA TCG GAA CTG GAG GAA CAA CTG ACC CCG      48
Lys Glu Leu Lys Ala Tyr Lys Ser Glu Leu Glu Glu Gln Leu Thr Pro
 1               5                  10                  15

GTG GCG GAG GAG ACG CGG GCA CGG CTG TCC AAG GAG CTG CAG GCG GCG      96
Val Ala Glu Glu Thr Arg Ala Arg Leu Ser Lys Glu Leu Gln Ala Ala
             20                  25                  30

GAG GCC CCG CTG GGC GCG GAC ATG GAG GAC GTG CGC GGC CGC CTG GTG     144
Glu Ala Pro Leu Gly Ala Asp Met Glu Asp Val Arg Gly Arg Leu Val
         35                  40                  45

CAG TAC CGC GGC GAG GTG CAG GCC ATG CTC GGC CAG AGC ACC GAG GAG     192
Gln Tyr Arg Gly Glu Val Gln Ala Met Leu Gly Gln Ser Thr Glu Glu
     50                  55                  60

CTG CGG GTG CGC CTC GCC TCC CAC CTG CGC AAG CTG CGT AAG CGG CTC     240
Leu Arg Val Arg Leu Ala Ser His Leu Arg Lys Leu Arg Lys Arg Leu
 65                  70                  75                  80

CTC CGC GAT GCC GAT GAC CTG CAG AAG CGC CTG GCA GTG TAC CAG GCC     288
Leu Arg Asp Ala Asp Asp Leu Gln Lys Arg Leu Ala Val Tyr Gln Ala
                 85                  90                  95

GGG GCC CGC GAG GGC GCC GAG CGC GGC CTC AGC GCC ATC CGC             330
Gly Ala Arg Glu Gly Ala Glu Arg Gly Leu Ser Ala Ile Arg
             100                 105                 110
```

(2) INFORMATION FOR SEQ ID NO:7:

(i) SEQUENCE CHARACTERISTICS:
        (A) LENGTH: 110 amino acids
        (B) TYPE: amino acid
        (D) TOPOLOGY: linear     (ii) MOLECULE TYPE: protein     (xi) SEQUENCE DESCRIPTION: SEQ ID NO:7:

```
Lys Glu Leu Lys Ala Tyr Lys Ser Glu Leu Glu Glu Gln Leu Thr Pro
 1               5                  10                  15

Val Ala Glu Glu Thr Arg Ala Arg Leu Ser Lys Glu Leu Gln Ala Ala
             20                  25                  30

Glu Ala Pro Leu Gly Ala Asp Met Glu Asp Val Arg Gly Arg Leu Val
         35                  40                  45

Gln Tyr Arg Gly Glu Val Gln Ala Met Leu Gly Gln Ser Thr Glu Glu
```

|  | 50 | 55 | 60 |
|---|---|---|---|
| Leu Arg Val Arg Leu Ala Ser His Leu Arg Lys Leu Arg Lys Arg Leu | | | |
| 65 | 70 | 75 | 80 |
| Leu Arg Asp Ala Asp Asp Leu Gln Lys Arg Leu Ala Val Tyr Gln Ala | | | |
|  | 85 | 90 | 95 |
| Gly Ala Arg Glu Gly Ala Glu Arg Gly Leu Ser Ala Ile Arg | | | |
|  | 100 | 105 | 110 |